(12) United States Patent
Beckman

(10) Patent No.: US 9,364,647 B1
(45) Date of Patent: Jun. 14, 2016

(54) SHUNT CATHETER SYSTEM

(71) Applicant: Joshua Marshall Beckman, Tampa, FL (US)

(72) Inventor: Joshua Marshall Beckman, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/744,842

(22) Filed: Jun. 19, 2015

Related U.S. Application Data

(60) Provisional application No. 62/030,946, filed on Jul. 30, 2014.

(51) Int. Cl.
*A61M 5/00* (2006.01)
*A61M 27/00* (2006.01)

(52) U.S. Cl.
CPC .......... *A61M 27/006* (2013.01); *A61M 2205/75* (2013.01); *A61M 2205/7545* (2013.01); *A61M 2205/7563* (2013.01)

(58) Field of Classification Search
CPC ..... A61M 1/00; A61M 27/00; A61M 27/006; A61M 2202/0464; A61M 2205/75; A61M 2205/7545; A61M 2205/7563
USPC .................................................... 604/8, 9, 10
See application file for complete search history.

(56) References Cited

U.S. PATENT DOCUMENTS

| | | | |
|---|---|---|---|
| 3,111,125 A * | 11/1963 | Schulte ............... | A61M 27/006 137/848 |
| 3,690,323 A | 9/1972 | Wortman et al. | |
| 4,583,967 A | 4/1986 | Harris | |
| 4,741,730 A | 5/1988 | Dormandy, Jr. et al. | |
| 5,437,626 A | 8/1995 | Cohen et al. | |
| 5,531,673 A | 7/1996 | Helenowski | |
| 8,088,091 B2 * | 1/2012 | Thomas ............... | A61M 27/006 604/540 |
| 2012/0060622 A1 | 3/2012 | Harris et al. | |

OTHER PUBLICATIONS

Ventureyra and Higgins. A New Ventricular Catheter for the Prevention and Treatment of Proximal Obstruction in Cerebrospinal Fluid Shunts. Neurosurgery. 1994. vol. 34 (No. 5): 924-26.
Reynolds et al., Adenocarcinoma Cells Trapped on a Millipore Filter in a Patient with Meningeal Carcinomatosis. Neurosurgery. 1980. Volume 7 (No. 2 ): 179-81.
Al-Tamimi et al., Ventriculoperitoneal Shunt 30-Day Failure Rate. Neurosurgery. 2014. vol. 74: 29-34.

(Continued)

*Primary Examiner* — Philip R Wiest

(74) *Attorney, Agent, or Firm* — Nilay J. Choksi; Smith & Hopen, P.A.

(57) ABSTRACT

A shunt catheter system and method of use thereof. The system generally includes an open-ended ventricular catheter with drainage apertures and safety flap valves, a reservoir with inline filter, and a peritoneal catheter. After insertion, for example into the ventricles of the brain, cerebrospinal fluid would pass into the ventricular catheter, through the inline filter in the reservoir, and into the peritoneal catheter, subsequently exiting the shunt catheter system. During insertion of the ventricular catheter, a catheter stylet or wire/string and plug stylet can be positioned therein to occlude the open end. The ventricular catheter may be positioned perpendicular to the peritoneal catheter and can be coupled to one another through the reservoir and inline filter or valve.

8 Claims, 4 Drawing Sheets

(56) References Cited

OTHER PUBLICATIONS

Stone et al., Revision Rate of Pediatric Ventriculoperitoneal Shunts after 15 Years. Journal of Neurosurgery Pediatrics. 2013. vol. 11: 15-19.

Reddy. Ventriculoperitoneal Shunt Surgery and the Incidence of Shunt Revision in Adult Patients with Hemorrhage-related Hydrocephalus. Clinical Neurology and Neurosurgery. 2012. vol. 114: 1211-216.

Chittiboina et al., Posthemorrhagic Hydrocephalus and Shunts: What Are the Predictors of Multiple Revision Surgeries? Journal of Neurosurg Pediatrics. 2013. vol. 11: 37-42.

Reddy et al., Management of Adult Hydrocephalus with Ventriculoperitoneal Shunts: Long-term Single-Institution Experience. Neurosurgery. 2011. vol. 69 (No. 4): 774-81.

Reddy et al., Long-Term Outcomes of Ventriculoperitoneal Shunt Surgery in Patients with Hydrocephalus. World Neurosurgery. 2014. vol. 81 (No. 2): 404-410.

O'Kelly et al., Shunt-dependent Hydrocephalus after Aneurysmal Subarachnoid Hemorrhage: Incidence, Predictors, and Revision Rates. Journal of Neurosurgery. 2009. vol. 111: 1029-035.

Harris and McAllister, II. Does Drainage Hole Size Influence Adhesion on Ventricular Catheters? Child's Nervous System. 2011. vol. 27: 1221-232.

Thomale et al., Perforation Holes in Ventricular Catheters—is Less More? Child's Nervous System. 2010. vol. 26: 781-89.

Harris et al., Mechanical Contributions to Astrocyte Adhesion Using a Novel in Vitro Model of Catheter Obstruction. Experimental Neurology. 2010. vol. 222: 204-10.

Harris and McAllister, II. What We Should Know About the Cellular and Tissue Response Causing Catheter Obstruction in the Treatment of Hydrocephalus. Neurosurgery. 2012. vol. 70: 1589-1602.

Cozzens et al., Increased risk of distal ventriculoperitoneal shunt obstruction associated with slit valves or distal slits in the peritoneal catheter. Journal of Neurosurgery. 1997. vol. 87: 682-86.

Lin et al., Computational and Experimental Study of Proximal Flow in Ventricular Catheters. Journal of Neurosurgery. 2003. vol. 99: 426-31.

Cheatle et al., Flow Characteristics of Cerebrospinal Fluid Shunt Tubing. Journal of Neurosurg: Pediatrics. 2012. vol. 9: 191-97.

Tal et al., Comparison of Side Hole versus Non Side Hole High Flow Hemodialysis Catheters. Hemodialysis International. 2006. vol. 10: 63-67.

Gruber and Roehrig. Prevention of Ventricular Catheter Obstruction and Slit Ventricle Syndrome by the Prophylactic Use of the Integra Antisiphon Device in Shunt Therapy for Pediatric Hypertensive Hydrocephalus: A 25-year Follow-up Study. Journal of Neurosurgery: Pediatrics. 2010. vol. 5: 4-16.

Takahashi et al., Ultrastructure of Obstructive Tissue in Malfunctioning Ventricular Catheters Without Infection. Neurol Med Chir (Tokyo). 1998. vol. 38: 399-404.

\* cited by examiner

SHUNT CATHETER SYSTEM

CROSS-REFERENCE TO RELATED APPLICATIONS

This nonprovisional application is a continuation of and claims priority to U.S. Provisional Patent Application No. 62/030,946, entitled "Shunt Catheter System with Inline Filter and Method of Use Thereof", filed Jul. 30, 2014 by the same inventor, the entirety of which is incorporated herein by reference.

BACKGROUND OF THE INVENTION

1. Field of the Invention

This invention relates, generally, to catheters. More specifically, it relates to open-ended shunt catheter systems with inline filters.

2. Brief Description of the Prior Art

Hydrocephalus is one of the most common pathologies encountered in neurosurgery. On average, 6,000 new babies are born with hydrocephalus every year, including two of every 1,000 babies born in the United States, and thousands of people are diagnosed later in childhood or as adults.

Over $1 billion is spent each year in the U.S. for the treatment of hydrocephalus. The primary treatment of hydrocephalus is cerebrospinal fluid diversion with a ventricular shunt (e.g., ventriculoperitoneal shunts are placed daily in a pediatric neurosurgery practice). In other words, cerebrospinal fluid shunts are positioned to supplement or replace lost drainage capacity. Over 36,000 shunt surgeries are performed each year in the U.S., and over two-thirds are not the first surgery for that particular patient. The total cost of shunts in the U.S. exceeds $2 billion per year, and this does not include the cost of any rehabilitative therapy or educational recommendations. Shunts are life-saving devices but are notorious for high failure rates, difficulty of diagnosing failure, and limited control options. The malfunction rate of these shunts is upward of 40%. The majority of malfunctions occur due to obstruction of the proximal catheter.

Currently catheters are designed as a closed-tube like structure with small drainage holes on the distal end. These drainage holes are small because they prevent large particles from entering the system to possibly obstruct the valve. The problem with this design is that they can be easily obstructed externally by choroid plexus, blood clot, or protein.

Shunts are known and have been described extensively in the art. Examples include U.S. Pat. No. 5,437,626 to Cohen et al.; U.S. Pat. No. 4,741,730 to Dormandy et al.; U.S. Patent App. Pub. No. 2012/0060622 to Harris et al.; U.S. Pat. No. 8,088,091 to Thomas et al.; U.S. Pat. No. 3,690,323 to Wortman et al.; U.S. Pat. No. 4,583,967 to Harris; U.S. Pat. No. 5,531,673 to Helenowski; Reynolds, A. F., P. R. Weinstein, and P. C. Johnson. "Adenocarcinoma Cells Trapped on a Millipore Filter in a Patient with Meningeal Carcinomatosis." Neurosurgery 7.2 (1980): 179-81; Al-Tamimi, Yahia Z., Priyank Sinha, Paul D. Chumas, Darach Crimmins, James Drake, John. Kestle, Richard Hayward, Guirish A. Solanki, Simon Thomson, and John Thorne. "Ventriculoperitoneal Shunt 30-Day Failure Rate." Neurosurgery 74.1 (2014): 29-34; Stone, Jonathan J., Corey T. Walker, Maxwell Jacobson, Valerie Phillips, and Howard J. Silberstein. "Revision Rate of Pediatric Ventriculoperitoneal Shunts after 15 Years." Journal of Neurosurgery: Pediatrics 11.1 (2013): 15-19; Reddy, G. Kesava. "Ventriculoperitoneal Shunt Surgery and the Incidence of Shunt Revision in Adult Patients with Hemorrhage-related Hydrocephalus." Clinical Neurology and Neurosurgery 114.9 (2012): 1211-216; Chittiboina, Prashant, Helena Pasieka, Ashish Sonig, Papireddy Bollam, Christina Notarianni, Brian K. Willis, and Anil Nanda. "Posthemorrhagic Hydrocephalus and Shunts: What Are the Predictors of Multiple Revision Surgeries?" Journal of Neurosurgery: Pediatrics 11.1 (2013): 37-42; Reddy, G. Kesava, Papireddy Bollam, Runhua Shi, Bharat Guthikonda, and Anil Nanda. "Management of Adult Hydrocephalus with Ventriculoperitoneal Shunts: Long-term Single-Institution Experience." Neurosurgery 69.4 (2011): 774-81; Reddy, G. Kesava, Papireddy Bollam, and Gloria Caldito. "Long-Term Outcomes of Ventriculoperitoneal Shunt Surgery in Patients with Hydrocephalus." World Neurosurgery (2013); O'kelly, Cian J., Abhaya V. Kulkarni, Peter C. Austin, David Urbach, and M. Christopher Wallace. "Shunt-dependent Hydrocephalus after Aneurysmal Subarachnoid Hemorrhage: Incidence, Predictors, and Revision Rates." Journal of Neurosurgery 111.5 (2009): 1029-035; Harris, Carolyn A., and James P. Mcallister. "Does Drainage Hole Size Influence Adhesion on Ventricular Catheters?" Child's Nervous System 27.8 (2011): 1221-232; Thomale, Ulrich W., Henning Hosch, Arend Koch, Matthias Schulz, Giesela Stoltenburg, Ernst-Johannes Haberl, and Christian Sprung. "Perforation Holes in Ventricular Catheters—is Less More?" Child's Nervous System 26.6 (2010): 781-89; Harris, Carolyn A., James H. Resau, Eric A. Hudson, Richard A. West. Candice Moon, and James P. Mcallister. "Mechanical Contributions to Astrocyte Adhesion Using a Novel in Vitro Model of Catheter Obstruction." Experimental Neurology 222.2 (2010): 204-10; Harris, Carolyn A., and James P. Mcallister. "What We Should Know About the Cellular and Tissue Response Causing Catheter Obstruction in the Treatment of Hydrocephalus." Neurosurgery (2012): 1; Ventureyra, Enrique C.g., and Michael J. Higgins. "A New Ventricular Catheter for the Prevention and Treatment of Proximal Obstruction in Cerebrospinal Fluid Shunts." Neurosurgery 34.5 (1994): 924-26; Lin, Julian, Martin Morris, William Olivero, Frederick Boop, and Robert A. Sanford. "Computational and Experimental Study of Proximal Flow in Ventricular Catheters." Journal of Neurosurgery 99.2 (2003): 426-31; Cheatle, Joseph T., Alexis N. Bowder, Sandeep K. Agrawal, Michael D. Sather, and Leslie C. Hellbusch. "Flow Characteristics of Cerebrospinal Fluid Shunt Tubing." Journal of Neurosurgery: Pediatrics 9.2 (2012): 191-97; Tal, Michael G., Aldo J. Peixoto, Susan T. Crowley, Neil Denbow, Donna Eliseo, and Jeffrey Pollak. "Comparison of Side Hole versus Non Side Hole High Flow Hemodialysis Catheters." Hemodialysis International 10.1 (2006): 63-67; Gruber, Rolf W., and Bernd Roehrig. "Prevention of Ventricular Catheter Obstruction and Slit Ventricle Syndrome by the Prophylactic Use of the Integra Antisiphon Device in Shunt Therapy for Pediatric Hypertensive Hydrocephalus: A 25-year Follow-up Study." Journal of Neurosurgery: Pediatrics 5.1 (2010): 4-16; Takahashi, Yoshihiko, Akira Ohkura, Masaru Hirohata, Takashi Tokutomi, and Minoru Shigemori. "Ultrastructure of Obstructive Tissue in Malfunctioning Ventricular Catheters Without Infection." Neurologia Medico-chirurgica 38.7 (1998): 399-404; and Jeffrey W. Cozzens et al., Increased risk of distal ventriculoperitoneal shunt obstruction associated with slit valves or distal slits in the peritoneal catheter, Journal of Neurosurgery, November 1997, Vol. 87, No. 5, Pages 682-686. Each of the foregoing references either include or describe the drawbacks of the prior art, namely (1) a closed distal end of the ventricular catheter, (2) ineffective filtering of the cerebrospinal fluid, and/or (3) continued malfunction rates being unacceptably high.

Accordingly, what is needed is a more effective shunt catheter to allow for better flow without occlusion while still maintaining a filtration system to prevent the valve from being obstructed. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved, more effective shunt catheter system is now met by a new, useful, and nonobvious invention.

In an embodiment, the current invention is a shunt catheter system for drainage of a fluid. The system includes a ventricular catheter having a proximal portion, a distal portion, and a longitudinal extent therebetween, where the distal portion includes an open distal end so that an interior of the ventricular catheter is in open communication with an external environment of the ventricular catheter through the open distal end. The system further includes a reservoir having a base and a hemispherical dome. The hemispherical dome is connected to a top surface of the reservoir base and has a bias toward being inflated but can be deflated when pressed. The proximal portion of the ventricular catheter is connected to the reservoir so that the interior of the ventricular catheter is in fluid communication with the interior of the reservoir. The system further includes a peritoneal catheter having a proximal end, a distal end, and a longitudinal extent therebetween, where the proximal end of the peritoneal catheter is coupled to the reservoir. With this structure, the fluid being drained follows a path of travel through the open distal end of the ventricular catheter, through the ventricular catheter itself, into the reservoir, and through the peritoneal catheter prior to being drained/flushed out.

The system may further include an inline filter positioned in the reservoir, where the inline filter has vertically-oriented apertures positioned along a perimeter of the filter so that the interior of the reservoir is in fluid communication with the interior of the peritoneal catheter through at least one of the apertures. The peritoneal catheter has a diameter that is parallel to a diameter of the filter aperture. Optionally, the inline filter may include a flange extending from the open top of the filter, where the flange would rest atop the top surface of the reservoir base and substantially perpendicular to the filter apertures.

The system may further include an occluding component extendable through the longitudinal extent of the ventricular catheter for occluding the open distal end of the ventricular catheter during insertion of the ventricular catheter. The occluding component has a rounded distal end. In an embodiment, the occluding component is a catheter stylet having a proximal end and a distal end, where the rounded distal end occludes the open distal end of the ventricular catheter. The catheter stylet includes a stopper for preventing the catheter stylet from extending excessively beyond the open distal end of the ventricular catheter. In an alternate embodiment, the occluding component is a wire and plug assembly having a proximal end and a rounded distal plug, where the assembly includes a wire extending proximally from the rounded distal plug. The assembly further includes a safety clip for preventing the rounded distal plug from extending excessively beyond the open distal end of the ventricular catheter.

The system may further include a plurality of safety flap valves located on the distal portion of the ventricular catheter. Each safety flap valve is hingedly connected to a wall of the ventricular catheter, so that the safety flap valve can hinge into the interior of the ventricular catheter resulting from a force placed on the outside of the safety flap valve. Further, the system can include a plurality of drainage apertures located on the distal portion of the ventricular catheter. The drainage apertures provide open communication between the interior of the ventricular catheter and the external environment.

In varying embodiments, the current invention is a shunt catheter system for drainage of a fluid. The shunt catheter system includes any combination of the foregoing structural and functional characteristics.

In an embodiment, the current invention is a shunt catheter system for drainage of cerebrospinal fluid from ventricles of a brain of a patient.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
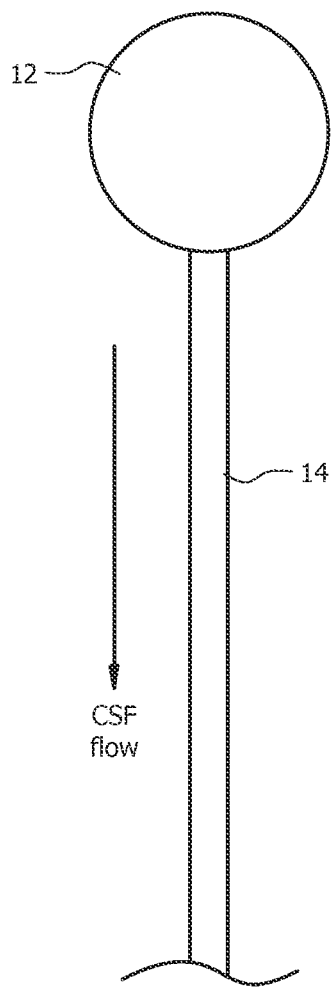
FIG. 1 is a top view of a shunt catheter system according to an embodiment of the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Open-Ended

In an embodiment, the current invention is a shunt catheter system. The shunt catheter system can be used for external ventricular drains or proximal shunt catheters. As opposed to conventional catheter systems that have closed-tube structures with small drainage holes on the distal end to prevent clogging by larger materials entering), the current invention contemplates that in certain embodiments, the drainage holes can be enlarged substantially. Further, it is contemplated herein that the structure of the shunt catheter system is an open-end tube, rather than a closed-end tube as in the conventional art. The shunt catheter system also incorporates the use of safety valves built within the catheter to allow an influx of fluid if the drainage holes become occluded, so that this fluid can be used to reopen the primary drainage holes.

Having an open-end tube would significantly increase the surface area for drainage. It would also allow a user/operator to "flush" the catheter clean, which is currently not possible. Conventional catheters are closed-end tubes because the catheters must pass through the brain, and this cannot be done with an open tube design because an open tube would fill with brain matter; as such, conventional shunt catheter systems have all intentionally used closed-tube designs and teach away from the disclosure of the current invention.

Stylet or Plug

In certain embodiments, however, in order to maintain an open-end tube while still preventing brain matter from entering the tube during insertion, the current invention includes a stylet or plug positioned within and along the ventricular catheter, where the stylet occludes the open distal end and can be withdrawn once the catheter is in the appropriate position. Essentially the stylet would provide similar properties to those of a closed tube shunt on insertion but is withdrawn after insertion in order to provide a larger-sized drainage hole than conventional shunt catheters have contemplated. Upon removal of the stylet from the ventricular catheter, the reservoir and peritoneal catheter can be coupled to the ventricular catheter as known in the art.

Further, the stylet can be structured to stop at the exact proper position every time within the ventricular catheter, so the stylet does not extend further through the open distal end than is necessary or desired. This can be accomplished using a stopper flange, safety clips, or other suitable structure. If the stylet is forced past this stopping point, though, it can be easily withdrawn proximally into the catheter, and the appropriate stopping point may be reached again. Using this catheter design allows the surgeon to continue using standard surgical tools, such as the neuropen or bugbee, if needed.

Filtration & Reservoir

With regards to the filtration issue experienced by conventional shunt catheter systems, the current shunt catheter system may include an inline filter to keep large particles from occluding the shunt valve. This inline filter would function similar to an inline fuel or water filter. It is contemplated that this filter can include apertures of any shape, though typically round, and having a larger surface area so that occlusion can be effectively prevented. It is contemplated herein that the ventricular catheter is not required to be used in conjunction with the reservoir/filter. They are separate entities and may be employed individually or in combination at the user's discretion. The reservoir component can also function as a tapping reservoir where a needle can be inserted transcutaneously to withdraw fluid for testing or other purposes. The inline filter may be incorporated into the reservoir. This will become clearer as this specification continues.

The inline filter connects directly to the peritoneal catheter and can function similar to a tapping reservoir. However, inside this reservoir may be a filter around the circumference of an inner larger bore, where the filter drains into the outlet. This outlet may or may not be connected to a valve.

The filter can also function as a "pumping reservoir", meaning that the filter or reservoir can be depressed with the user's finger or other instrument (similar to a valve reservoir) to pump the fluid. This structure and functionality allows the ventricular catheter to be flushed out. If a conventional closed-end catheter was flushed in a similar manner, the material would just be pushed to the base without actually pushing it out of the system. Contrastingly, when this catheter is flushed, debris can actually be pushed out of the catheter.

This can be achieved by the distal end of the ventricular catheter including a plurality of drainage apertures and safety flap valves. The safety flap valves would allow fluid to enter the pumping reservoir when the drainage holes of the ventricular catheter are occluded so that debris could be flushed out. The flap valves could also function to keep the catheter system functional in an emergency situation in which the debris could not be cleared. Essentially, the pumping reservoir would draw fluid into the catheter from the negative pressure created in the system (pushing down on the "pumping reservoir" and releasing). Then, when it was pushed again, the fluid would be pushed downstream through the peritoneal catheter, and more fluid would be drawn into the system. Also, the safety flap valves can be any size or shape and be designed to open with under specific amounts of pressure (e.g., 20 cm/$h_2o$), depending on the cut and material used.

The system permits flushing of the system transcutaneously with no increased risk of infection, as discussed previously. This system also applies to external ventricular drains and has the potential to reduce their malfunction rate to zero. This is particularly important with placement of drains in patients with intraventricular hemorrhage where they can become obstructed with blood clot. The system allows for the physician to clear the external ventricular drain (EVD) without having to place an entire new system and without having to use hemolytic agents that could cause further brain hemorrhage, resulting in greater safety and less risk for the patient. This design will be compatible with all systems currently in use, including both EVD collection kits and shunt systems.

An exemplary application of the current system is in the field of critical care medical devices for treatment of hydrocephalous.

Example

As seen in FIGS. 1 and 2A-2C, the current invention is a shunt catheter system, generally denoted by the reference numeral 10, that includes reservoir 12, peritoneal catheter 14, open-ended ventricular catheter 16. Ventricular catheter 16 has proximal end 18a and distal end 18b. Distal end 18b of ventricular catheter 16 includes open end 19. Reservoir 12 may include reservoir base 12a having top surface 12b, and flexible dome 12c. Reservoir 12 may further include inline filter 20, which will be described in further detail as this specification continues.

As used herein, the term "proximal" refers to a relative position closer to a reservoir component of the overall assembly. The term "distal" refers to a relative position further from the reservoir component of the overall assembly. As such, if the goal of the system is to drain cerebrospinal fluid from the brain, for example, the cerebrospinal fluid would travel proximally from the brain to the reservoir component and then distally from the reservoir component to the peritoneum through the peritoneal cavity.

Figures 2A, 2B, 2C:
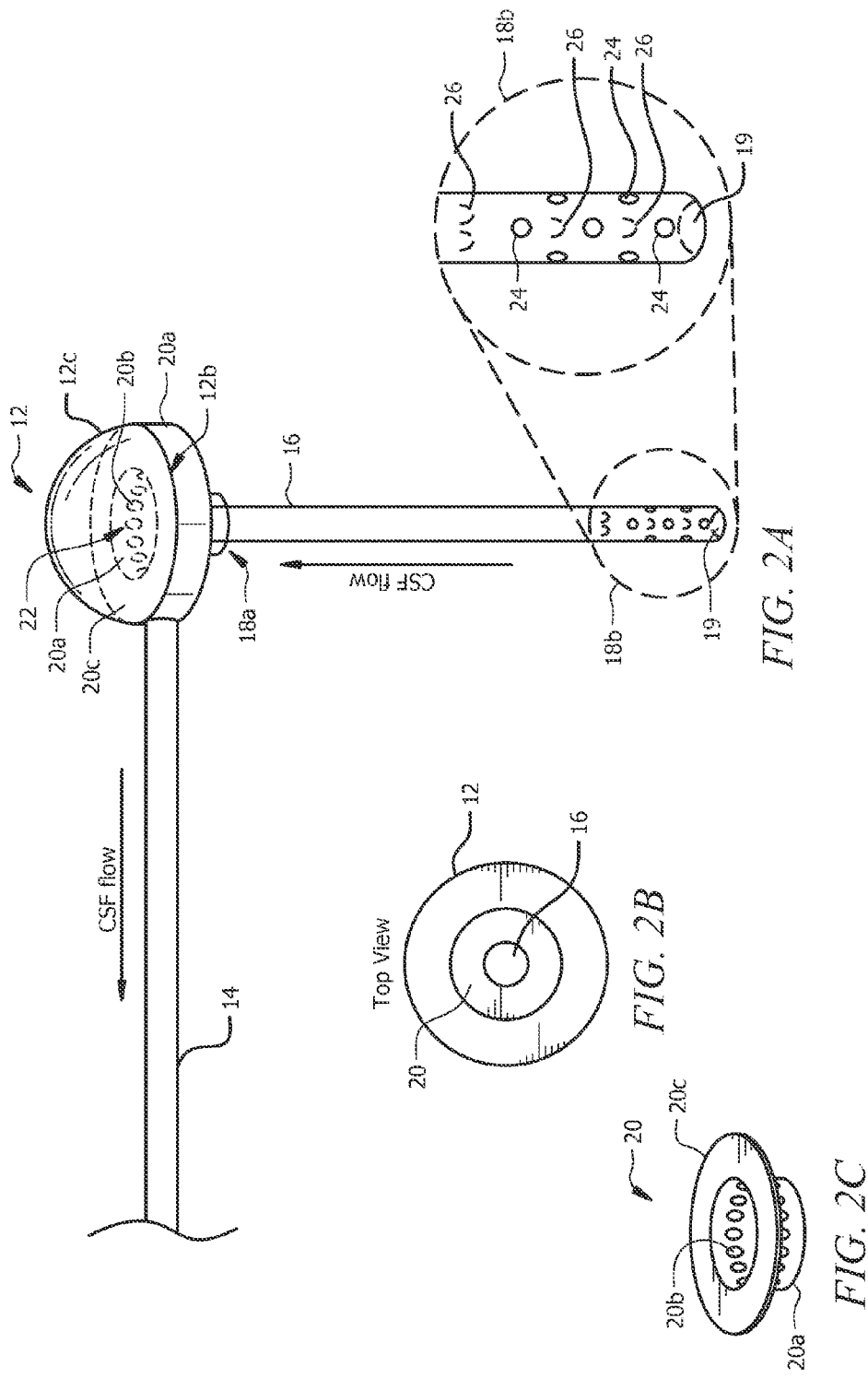
FIG. 2A is perspective view of a shunt catheter system according to an embodiment of the current invention.
FIG. 2B is a close-up perspective view of a filter within the shunt catheter system of FIG. 2A.
FIG. 2C is a close-up top view of a reservoir within the shunt catheter system of FIG. 2A.

Further, relative positioned will be described as illustrated in FIG. 2A. For example, the terms "top" and "bottom" can be used to described structures associated within the system as it can be seen in FIG. 2A, but it should be understood that the system can be positioned in any way such that the terms "top" and "bottom" for example no longer literally refer to the top of the system and the bottom of the system. However, these positional terms will be used herein for clarity in describing the structural relationship among the components of the system.

After insertion of system 10 into a patient or subject, for example with ventricular catheter 16 inserted into the ventricles of the brain, cerebrospinal fluid would follow a path of travel proximally through ventricular catheter 16, through inline filter 20 and reservoir 12, and distally through peritoneal catheter 12, finally exiting shunt catheter system 10 into the peritoneum of the patient or subject. It is contemplated herein, however, that ventricular catheter 16 can be connected directly to a conventional valve assembly (not shown) without reservoir 12, filter 20, and peritoneal catheter 14, based on the user or surgeon's preference.

Structurally, FIG. 1 depicts an assembly of reservoir 12 and peritoneal catheter 14, showing CSF flow in a distal direction if this distal assembly is utilized in shunt catheter system 10. Peritoneal catheter 14 is coupled to and extends from reservoir 12, such that the interior of peritoneal catheter 14 is in communication with the interior of reservoir 12. For example, peritoneal catheter can be coupled to reservoir 12 at reservoir base 12a, as can be seen in FIG. 2A. Peritoneal catheter 14 is aligned with inline filter 20, so that fluid passing through filter 20 flows distally through peritoneal catheter 14.

Still referring to FIG. 2A, ventricular catheter 16 can be coupled to reservoir 12 in any way to provide communication between the interior of ventricular catheter 16 and the interior of reservoir 12. For example, ventricular catheter 16 can be coupled to reservoir 12 at reservoir 12a. In an embodiment, the longitudinal extent of ventricular catheter 16 is positioned substantially perpendicular to the longitudinal extent of peritoneal catheter 12 when proximal end 18a of ventricular catheter 16 is coupled to the bottom surface of reservoir base 12a (see FIG. 2A). Thus, peritoneal catheter 14 and ventricular catheter 16 are indirectly coupled to each other through reservoir 12 and inline filter 20. Proximal end 18a of ventricular catheter 16 enters reservoir 12 in base 12a of reservoir 12, thus feeding fluid into the interior of reservoir 12 and through inline filter 20 into the proximal end of peritoneal catheter 14.

Reservoir can also include a hemispherical, flexible dome 12c coupled to top surface 12b of reservoir base 12a of reservoir 12. Dome 12c can be depressed forcibly (e.g., via a user's finger or other instrument), thus allowing reservoir 12 to function as a "pumping reservoir." Depression of reservoir dome 12c would pump fluid into peritoneal catheter 14, while subsequent inflation of reservoir dome 12c (by releasing reservoir dome 12c) would create negative pressure to draw fluid from ventricular catheter 16 into the interior of reservoir 12 and inline filter 20. Occluding peritoneal catheter 14 with the user's finger or other instrument would force fluid back into ventricular catheter 16. This structure and functionality allows ventricular catheter 16 to be flushed out.

Now referring to FIG. 2B, which is a top view of reservoir 12, shows a particular configuration of reservoir 12, ventricular catheter 16, and filter 20. In this configuration, reservoir 12 has the largest diameter, filter 20 has a diameter smaller than the diameter of reservoir 12, and ventricular catheter 16 has a diameter smaller than the diameter of filter 20. Thus, ventricular catheter 16 has a first diameter, filter 20 has a second diameter, and reservoir 12 has a third diameter, where the first diameter is smaller than the second and third diameters and the second diameter is smaller than the third diameter. Filter 20 is contained within reservoir 12, and ventricular catheter 16 is in communication with reservoir 12 and filter 20.

With regards to the structure of filter 20 itself, as seen in FIG. 2C, and its implementation in reservoir 12, as seen in FIG. 2A, filter 20 is cylindrically-shaped with open top 22 and an open bottom. From ventricular catheter 16, fluid enters the interior of reservoir 12 through the open bottom and opening 22. Filter 20 includes vertical sidewall 20a, a plurality of filtration apertures 20b, and top flange 20c. Filtration apertures 20b are disposed along the circumference of vertical sidewall 20a of cylindrically-shaped filter 20. Filtration apertures 20b are vertically-oriented (i.e., their diameters are perpendicular to the longitudinal extent of peritoneal catheter 14) and may be any size or shape for blocking larger materials from entering peritoneal catheter 14. Inline filter 20 may also include top flange 20c extending outwardly and perpendicularly from vertical sidewall 20a of filter 20 along open top 22 of filter 20. This helps direct the fluid through filtration apertures 20b of filter 20 into peritoneal catheter 14. Inline filter 20 prevents large particles from occluding the shunt valve.

Top flange 20c may also be needed if filter 20 is to be removable from reservoir 12, as top flange 20c provides stability within reservoir 12. Alternatively, it is contemplated herein that filtration apertures 20b can be built directly into reservoir 12 when vertical sidewall 20a is integrated within reservoir 12.

Still referring to FIG. 2A, distal end 18b of ventricular catheter 16 includes open end 19 and may include a plurality of drainage apertures 24 and safety flap valves 26. Along with open end 19, drainage apertures 24 positioned in proximity thereto also permits greater surface area for drainage. Alternatively, open end 19 may include only safety flap valves 26 and no drainage apertures 24.

Figure 3A:
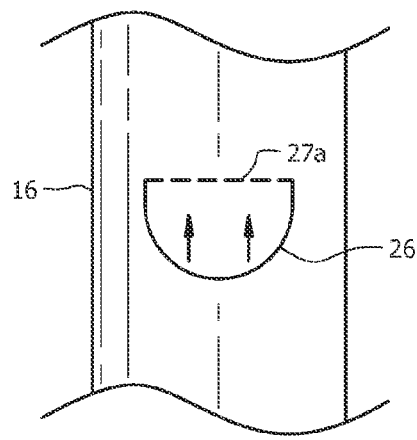
FIG. 3A is a close-up view of a safety flap valve within a ventricular catheter of a shunt catheter system according to an embodiment of the current invention.
Figure 3B:
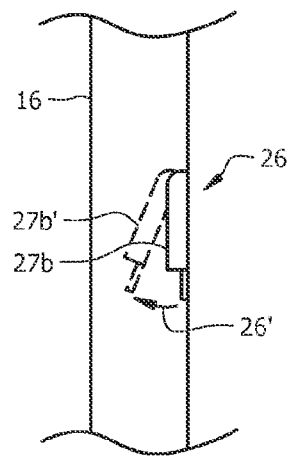
FIG. 3B is a cross-sectional side view of the safety flap valve of FIG. 3A.

FIGS. 3A-3B are close-up views of the structure and function of safety flap valve 26 typically positioned along distal end 18b of ventricular catheter 16 near open end 19. Safety flap valves 26 are spaced between and among (e.g., 1 cm) drainage apertures 24. In an embodiment, safety flap valves 26 may be positioned above drainage apertures 24 in a circumferential fashion to best allow drainage in the event of an obstruction. The location, size, and quantity can vary extensively depending on the desired result.

The purpose of safety flap valves 26 is to allow fluid flow in the event of an obstruction of open end 19 and/or drainage apertures 24. Rather than simply including a greater number of drainage apertures, safety flap valves 26 can be used because fluid flow through an aperture (i.e., turbulence) can cause obstruction by either protein buildup or growth of choroid plexus. Safety flap valves 26 do not have open flow and thus can remain closed unless there is an obstruction, in which case a pressure gradient will cause safety flap valves 26 to open. Additionally, in the event of an obstruction, safety flap valves 26 can be used to draw fluid into ventricular catheter 16 (via a pumping mechanism) so that distal open end 19 can be flushed (while obstructing close to the valve).

Structurally, safety flap valve 26 includes side 27a (e.g., top side) that is attached to the wall of ventricular catheter 16 and has one or more other sides 27b, 27b' that are not connected to wall of ventricular catheter 16. Non-connected sides 27b, 27b' of safety flap valve 26 have a stable position in line with or otherwise parallel to the wall of ventricular catheter 16 (see stable position 27b). Upon a force being pushed on safety flap valve 26 from the exterior of ventricular catheter 16 or a negative pressure or "suction" force applied from pumping reservoir 12, as discussed previously, non-connected sides 27b, 27b' are biased to bend (in the direction of arrow 26') into the interior of ventricular catheter 16 (see biased position 27b'). Safety flap valves 26 are biased to resist bending out of ventricular catheter 16, by the cut or use of an extended flap, so that fluid will be forced out of ventricular catheter 16 through drainage apertures 24 rather than through safety flap valves 26 when flushing ventricular catheter 16.

If open end 19 and/or drainage apertures 26 are obstructed, then fluid may be drawn into ventricular catheter 16 and reservoir 12 through safety flap valves 26 either spontaneously through a pressure gradient or by the negative pressure created by pumping reservoir 12, so that system 10 maintains functionality even during distal obstruction. Safety flap valves 26 can thus be used to draw fluid into reservoir 12 and ventricular catheter 16. The fluid can then be flushed distally by occluding peritoneal catheter 14 (or by obstructing the catheter proximal to the valve) and depressing either a valve or reservoir 12, in order to open drainage apertures 24 and/or open end 19 that is/are occluded. This can all be accomplished without having to break the skin of the patient or subject. Without safety flap valves 26, there may be no ability to flush ventricular catheter 16 or bypass drainage apertures 24 to keep fluid flowing in the event of an obstruction.

Because distal end 18b of ventricular catheter 16 is open end 19, as opposed to closed as in the conventional art (in order to prevent brain matter from entering the ventricular catheter), open end 19 must be occluded during insertion of ventricular catheter 16 into the brain in order to prevent brain matter from entering ventricular catheter 16. FIGS. 4A-4F depict two exemplary manners of occluding open end 19 during insertion.

Figure 4A:
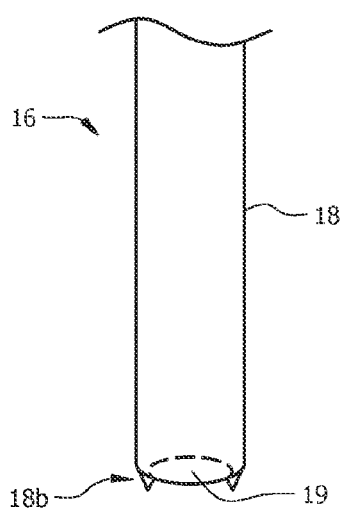
FIG. 4A is an elevated view of a catheter stylet according to an embodiment of the current invention.

FIG. 4A shows an unoccluded distal opening of a ventricular catheter.

Figure 4B:
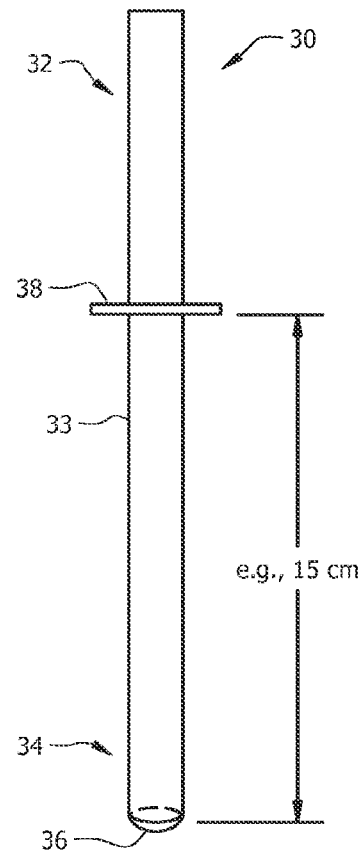
FIG. 4B is a top or end view of a string/wire and plug according to an embodiment of the current invention.
Figure 4C:
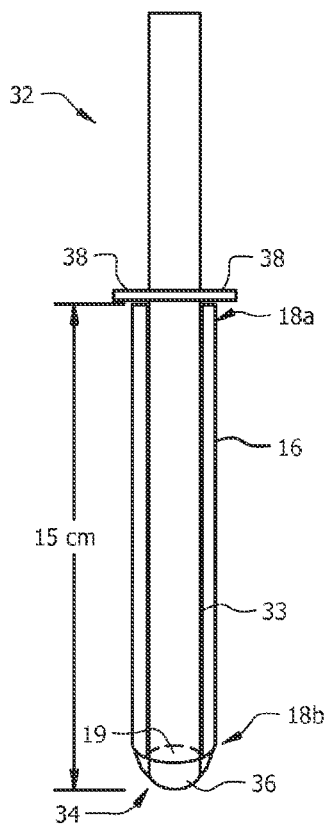
FIG. 4C is an elevated side view the string/wire and plug of FIG. 4B.

FIGS. 4B and 4C respectively depict a catheter stylet, generally denoted by the reference numeral 30, standing alone and catheter stylet 30 inserted into the hollow interior of ventricular catheter 16 in order to occlude open end 19. Catheter stylet 30 includes proximal end 32, body 33, distal end 34, and rounded closed end 36 along the edge of distal end 34. Catheter stylet 30 further includes stopper 38 disposed perpendicular to the longitudinal extent of catheter stylet 30. Stopper 38 allows catheter stylet 30 to be repeatedly inserted into the interior of ventricular catheter 16 to the same consistent distance (e.g., 15 cm which may be the length of the ventricular catheter itself).

This can be seen in FIG. 4C, where catheter stylet 30 is inserted into proximal end 18a of ventricular catheter 16 and is stopped at the proximal edge of ventricular catheter 16 via stopper 38. When this happens, body 33 is contained within ventricular catheter 16 and proximal end 32 is disposed outside of ventricular catheter 16. Further, rounded end 36 occludes open end 19 of ventricular catheter 16 on the opposite end in order to prevent damaging any tissue (e.g., brain tissue) during insertion of ventricular catheter 16. It should be noted that during insertion of ventricular catheter 16, reservoir 12 and peritoneal catheter 14 would not be coupled to ventricular catheter 16. Once ventricular catheter 16 is in proper position, catheter stylet 30 can be removed from ventricular catheter 16, and reservoir 12 and peritoneal catheter 14 can be coupled to ventricular catheter 16 (or alternatively, a valve assembly can be coupled to ventricular catheter 16).

Figure 4D:
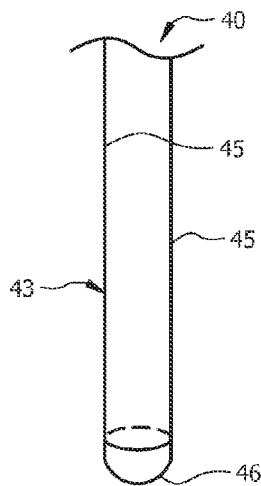
FIG. 4D is an elevated side view of a ventricular catheter.
Figure 4E:
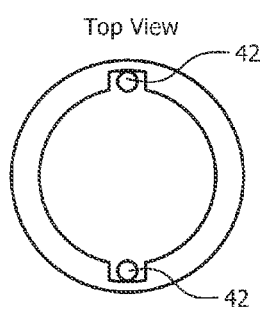
FIG. 4E depicts the string/wire and plug of FIGS. 4B-4C inserted into the ventricular catheter of FIG. 4D.
Figure 4F:
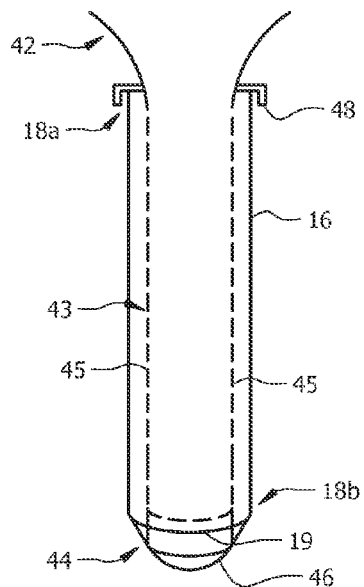
FIG. 4F depicts the catheter stylet of FIG. 4A inserted into the ventricular catheter of FIG. 4D.

FIGS. 4D-4F depict an alternative apparatus or method for distal opening (i.e., open end 19) occlusion. FIGS. 4D-4E depict a string/wire and plug stylet, generally denoted by the reference numeral 40, standing alone. FIG. 4F depicts string/wire and plug stylet 40 inserted into the hollow interior of ventricular catheter 16 in order to occlude open end 19. String/wire and plug stylet 40 can be employed in the event that a navigating stylet or any other standard shunt stylet is desired as they are designed for a "closed ended" catheter. Conventional stylets typically are square-ended (and would damage tissue during insertion) and do not extend entirely through the ventricular catheter. Thus, string/wire and plug stylet 40 can be inserted into the interior of ventricular catheter 16 first, followed by the conventional stylet, thus essentially extending the conventional stylet and giving it a rounded end.

String/wire and plug stylet 40 includes proximal end 42, body 43, distal end 44, and rounded plug 46 on distal end 44. Body 43 is formed of one or more strings/wires 45. Plug 48 can be rounded in order to prevent damaging any tissue (e.g., brain tissue) during insertion of ventricular catheter 16.

String/wire and plug stylet 40 further includes safety clips 48 on strings/wires 45. Safety clips 48 allow string/wire and plug stylet 40 to be repeatedly inserted into the interior of ventricular catheter 16 to the same consistent distance (e.g., 15 cm which may be the length of the ventricular catheter itself). It is contemplated herein that safety clips 48 may or may not span the diameter of ventricular catheter 16, meaning safety clip 48 may be semicircular or even be structured as a washer-type assembly with a central aperture that is the size of the internal diameter of ventricular catheter 16. In an embodiment with the washer-type assembly (a cross-section of which is indicated in FIG. 4F), the washer-type safety clip can have a diameter that is substantially equal to the internal diameter of ventricular catheter 16, thus providing an even channel through which the conventional catheter can be inserted. In other words, it is contemplated herein that safety clip 48 should not obstruct the proximal opening of ventricular catheter 16, as that would obstruct insertion of the conventional catheter.

This can be seen in FIG. 4F, where string/wire and plug stylet 40 is inserted into proximal end 18a of ventricular catheter 16 and is stopped at the proximal edge of ventricular catheter 16 via safety clips 48. When this happens, body 43 is contained within ventricular catheter 16 and proximal end 42 is disposed outside of ventricular catheter 16. Further, rounded plug 46 occludes open end 19 of ventricular catheter 16 on the opposite end in order to prevent damaging any tissue (e.g., brain tissue) during insertion of ventricular catheter 16. It should be noted that during insertion of ventricular catheter 16, reservoir 12 and peritoneal catheter 14 would not be coupled to ventricular catheter 16. Once ventricular catheter 16 is in proper position, string/wire and plug stylet 40 can be removed from ventricular catheter 16, and reservoir 12 and peritoneal catheter 14 can be coupled to ventricular catheter 16 (or alternatively, a valve assembly can be coupled to ventricular catheter 16).

Plug 46 is a removable component that is withdrawn or retrieved from the interior of ventricular catheter 16 by pulling strings/wires 45, which are attached to plug 46. Plug 46 is designed so that if plug 46 is unintentionally inserted through open end 19 (despite safety clips 48), plug 46 can be withdrawn back to the appropriate spot. When plug 46 is inserted into ventricular catheter 16 at open end 19, a standard shunt or navigation stylet (typically flat tipped without a stopper) (not shown) can be inserted into the hollow interior of ventricular catheter 16 with string/wire and plug stylet 40 in place. This allows the standard stylet to be used while keeping open end 19 occluded. Further, safety clips 48 prevent the standard stylet without a stopper to be pushed through open end 19 of ventricular catheter 16.

Once ventricular catheter 16 is placed in the desired position, the standard stylet is withdrawn and then plug 46 can be withdrawn by pulling out strings/wires 45, thus removing string/wire and plug stylet 40 from ventricular catheter 16, leaving only ventricular catheter 16 in place. This can be done together or separately.

Methodologically, shunt catheter system 10 described herein can be used as follows, as applied to the brain of a patient or subject. Prior to connection of reservoir 12 and peritoneal catheter 14 with ventricular catheter 16, ventricular catheter 16 (including catheter stylet 30 or string/wire and plug stylet 40) is inserted into the proper position in the ventricles of the brain (the ventricular catheter is pushed through brain parenchyma until reaching the cerebrospinal fluid filled cavity, i.e., the ventricle). Stylets 30, 40 function in keeping ventricular catheter 16 from coring out brain tissue. Once ventricular catheter 16 is positioned in the ventricle, then stylet 30, 40 can be withdrawn, so a large-diameter bore (i.e., open end 19 in distal end 18b of ventricular catheter 16) remains in distal end 18b of ventricular catheter 16. With ventricular catheter 16 in place, reservoir 12 (with peritoneal catheter 14) is then connected to proximal end 18a of ventricular catheter 16 without stylet 30, 40. Open end 19 can drain fluid into reservoir 12, and then, in turn, drain to a distal valve (not shown in the figures) and/or peritoneal catheter 14. Reservoir 12 can be pumped to draw fluid distally and also to flush out ventricular catheter 16.

GLOSSARY OF CLAIM TERMS

Catheter stylet: This term is used herein to refer to a probe inserted into a ventricular catheter within the body of a patient or subject for occluding an open end of that ventricular catheter.

Distal: This term is used herein to refer to a relative position further from the reservoir component of the overall assembly. If a reservoir is not present in the assembly, then it is a relative position closer to the target area of drainage.

Drainage aperture: This term is used herein to refer to an opening in a catheter, where the opening permits fluid to flow therethrough to the interior of the catheter.

Excessively beyond: This term is used herein to refer to a relative position of an occluding component near the distal opening of a catheter, where progression of the occluding component any further distally beyond the distal opening does not provide any further benefit from occlusion of the distal opening.

Hemispherical dome: This term is used herein to refer to a roof of the reservoir for containing any liquid contained therein.

Inline filter: This term is used herein to refer to an apparatus the separates larger particulates from a fluid, where the apparatus is aligned with the natural flow of the fluid within the overall assembly or system.

Occluding component: This term is used herein to refer to an apparatus with an end that blocks or obstructs a distal opening in the ventricular catheter.

Peritoneal catheter: This term is used herein to refer to a thin tube inserted into the body of a patient or subject to serve a surgical purpose. In particular here, the distal end of the catheter can be inserted into the peritoneum for drainage of a fluid.

Plug: This term is used herein to refer to a rounded component used to occlude an opening.

Proximal: This term is used herein to refer to a relative position closer to a reservoir component of the overall assembly. If a reservoir is not present in the assembly, then it is a relative position further from the target area of drainage.

Reservoir: This term is used herein to refer to a contained space where fluid can be held or through which fluid can be pumped.

Safety clip: This term is used herein to refer to an apparatus that prevents a plug assembly from progressing further distally in the ventricular catheter than is necessary for occluding the distal opening at the end of the ventricular catheter.

Safety flap valve: This term is used herein to refer to an apparatus that controls the flow of a fluid through a ventricular catheter.

Shunt catheter system: This term is used herein to refer to an assembly of at least one ventricular catheter, optionally in combination with a valve housing or reservoir, a filter, a peritoneal catheter, and a stylet.

Stopper: This term is used herein to refer to an apparatus that prevents a catheter stylet from progressing further distally in the ventricular catheter than is necessary for occluding the distal opening at the end of the ventricular catheter.

Ventricular catheter: This term is used herein to refer to a thin tube inserted into the body of a patient or subject to serve a surgical purpose. In particular here, the distal end of the catheter can be inserted into the ventricle of a brain for drainage of a fluid.

Vertically-oriented aperture: This term is used herein to refer to an opening with a length or diameter disposed along a vertical plane, relative to the remainder of the assembly or system as seen in FIG. 2A.

Wire and plug assembly: This term is used herein to refer to an apparatus inserted into a ventricular catheter within the body of a patient or subject for occluding an open end of that ventricular catheter, while also allowing a conventional flat-end stylet to be inserted into the ventricular catheter as well.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A shunt catheter system for drainage of a fluid, comprising:
   a ventricular catheter having a proximal portion, a distal portion, and a longitudinal extent therebetween, wherein said distal portion of said ventricular catheter terminates at an open distal end such that an interior of said ventricular catheter is in open communication with an external environment of said ventricular catheter through said open distal end; and
   a plurality of safety flap valves located on said distal portion of said ventricular catheter, said safety flap valves being hingedly connected to a wall of said ventricular catheter and biased against said wall, such that each safety flap valve can hinge into said interior of said ventricular catheter resulting from a force placed on the outside of said safety flap valve,
   whereby said fluid is configured to follow a path of travel from a ventricular cavity, through said open distal end and through said plurality of safety flap valves, and into said interior of said ventricular catheter.

2. A shunt catheter system as in claim 1, further comprising:
   a reservoir having a base and a hemispherical dome connected to a top surface of said base, said hemispherical dome having a bias toward being inflated but capable of being depressed upon a force being applied to said hemispherical dome,
   said proximal portion of said ventricular catheter coupled to said reservoir, such that said interior of said ventricular catheter is in fluid communication with an interior of said reservoir;
   a peritoneal catheter having a proximal end, a distal end, and a longitudinal extent therebetween, wherein said proximal end of said peritoneal catheter is coupled to said reservoir,
   whereby said fluid follows a path of travel through said open distal end and through said plurality of safety flap valves into said interior of said ventricular catheter, through said ventricular catheter and into said reservoir, and into said peritoneal catheter prior to being flushed out.

3. A shunt catheter system as in claim 1, further comprising:
   an inline filter positioned within said interior of said reservoir, said inline filter having a plurality of vertically-oriented apertures positioned along a perimeter of said inline filter, such that said interior of said reservoir is in fluid communication with an interior of said peritoneal catheter through an aperture of said plurality of vertically-oriented apertures, said peritoneal catheter having a diameter that is parallel to a diameter of said aperture.

4. A shunt catheter system as in claim 1, further comprising:
   an occluding component extendable through said longitudinal extent of said ventricular catheter for occluding said open distal end of said distal portion of said ventricular catheter during insertion of said ventricular catheter, said occluding component having a rounded distal end.

5. A shunt catheter system as in claim 4, further comprising:
   said occluding component being a catheter stylet having a proximal end and said rounded distal end,
   said catheter stylet including a stopper for preventing said catheter stylet from extending excessively beyond said open distal end of said ventricular catheter, such that said proximal end of said catheter stylet is disposed external to said ventricular catheter and said rounded distal end of said catheter stylet occludes said open distal end of said ventricular catheter.

6. A shunt catheter system as in claim 4, further comprising:
   said occluding component being a wire and plug assembly having a proximal end and a rounded distal plug, said wire and plug assembly including a wire extending proximally from said rounded distal plug,
   said wire and plug assembly including a safety clip for preventing said rounded distal plug from being disposed excessively beyond said open distal end of said ventricular catheter, such that said proximal end of said wire and plug assembly is disposed external to said ventricular catheter and said rounded distal plug of said wire and plug assembly occludes said open distal end of said ventricular catheter.

7. A shunt catheter system as in claim 6, further comprising:
   said safety clip having a central aperture disposed therein, said central aperture having a diameter that is substantially equal to an internal diameter of said ventricular catheter.

8. A shunt catheter system as in claim 1, further comprising:
   a plurality of drainage apertures located on said distal portion of said ventricular catheter,
   said plurality of drainage apertures providing open communication between said interior of said ventricular catheter and said external environment of said ventricular catheter.

* * * * *